US006815446B1

(12) United States Patent
Biaggioni et al.

(10) Patent No.: US 6,815,446 B1
(45) Date of Patent: Nov. 9, 2004

(54) SELECTIVE ANTAGONISTS OF A2B ADENOSINE RECEPTORS

(75) Inventors: Italo O. Biaggioni, Nashville, TN (US); Igor A. Feoktistov, Nashville, TN (US); Jack N. Wells, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/648,775

(22) Filed: Aug. 28, 2000

Related U.S. Application Data

(60) Provisional application No. 60/151,649, filed on Aug. 31, 1999.

(51) Int. Cl.[7] .................... C07D 473/06; A61K 31/522; A61P 1/12; A61P 25/24; A61P 29/00

(52) U.S. Cl. ............................... 514/263.2; 514/234.2; 514/263.34; 514/263.22; 544/272; 544/118

(58) Field of Search ................................ 514/263, 272; 6/514, 234.2, 263.34, 263.2, 263.22

(56) References Cited

U.S. PATENT DOCUMENTS

| | | | | |
|---|---|---|---|---|
| 4,089,959 | A | 5/1978 | Diamond | |
| 4,120,947 | A | 10/1978 | Diamond | |
| 4,325,956 | A | 4/1982 | Kjellin et al. | |
| 4,593,095 | A | 6/1986 | Snyder et al. | |
| 4,696,932 | A | 9/1987 | Jacobson et al. | |
| 4,804,664 | A | 2/1989 | Kjellin et al. | |
| 5,470,579 | A * | 11/1995 | Bonte et al. | 514/263 |
| 5,516,894 | A | 5/1996 | Reppert | |
| 5,641,784 | A | 6/1997 | Kufner-Muhl et al. | |
| 5,646,156 | A | 7/1997 | Jacobson et al. | |
| 5,670,498 | A | 9/1997 | Suzuki et al. | |
| 5,703,085 | A | 12/1997 | Suzuki et al. | |
| 5,776,960 | A | 7/1998 | Oppong et al. | |
| 5,780,481 | A | 7/1998 | Jacobson et al. | |
| 5,854,081 | A | 12/1998 | Linden et al. | |
| 5,877,180 | A | 3/1999 | Linden et al. | |
| 2003/0105077 | A1 * | 6/2003 | Kanstrup et al. | 544/272 |

FOREIGN PATENT DOCUMENTS

| | | |
|---|---|---|
| CA | 2064742 | 12/1991 |
| EP | 0 386 683 | 9/1990 |
| GB | 228733 | 11/1995 |
| WO | WO 92/00297 | 7/1992 |
| WO | WO 92/12260 | 7/1992 |
| WO | WO 93/23401 | 11/1993 |
| WO | WO 95/11681 | 5/1995 |

OTHER PUBLICATIONS

Auchampach JA, Mol. pharmacol. 52:846–860, 1997.*
Feoktistov J clin. Invest. 96:1979–1986, (1995).*
Feoktistov Pharmacol. Rev. 49:381–402, 1997.*
Feoktistov Trends Pharmacol.sci. 19: 148–153, (1998).*
Feoktistov Drug Dev Res. 45:198–206, 1998.*
Grant MB, Circ. Res. 85:699–706. (1999).*
Strohmeier J Biol. chem. 270:2387–2394 (1995).*
Feoktistov , Biochem. Pharm. 62, 1163 (2001).*
Katsushima, et al., "Structure–Activity Relationships of 8–Cycloalkyl–1,3–dipropylxanthines as Anatagonists of adenosine Receptors", *J. Med. Chem.* 33:1906–1910 (1990).
Martinson, et al., "Potent Adenosine Receptor Antagonists that are Selective for the $A_1$ Receptor Subtype", *Molecular Pharmacology*, 31:247–252 (1986).
Jacobsonh et al, "1,3–Dialkylxanthine Derivatives Having Potency as Antagonists at Human $A_{28}$ Adensione Receptors", *Drug Development Research*, 47:45–53 (1999).
Kleiner, "Reactions of Some 8–(3–Pyridyl)–6–thioxanthines with Methyl Iodide" 739–743 (1973).
Klotz, et al., "Comparative pharmacology of human adenosine receptors subtype–characterization of stably transfected recptors in CHO cells", *Nauny–Schmideberg's Arch Pharmacol*, 357:1–9 (1998).
Linden, et al., "Charcterization of Huamn $A_{1B}$ Adenosine Receptors: Radiolignad Binding, Western Blotting and Coupling to Gq in Human Embryonic Kidney 293 Cells and HMC–1 Mast Cells", *Molecular Pharmacology* 56:705–713 (1999).
Kim et al., "Acyl–Hydrazide Derivatives of a Xanthine Carboxylic Congener (Xcc) asSelective Antagonists at Human $A_{2b}$ Adenosine Receptors", *drug Development Research*, 47:178–188.
Erickson, et al., "1,3,8–Trisubstituted Xanthines. Effects of Substitution Pattern upon Adenosine Receptor $A_1/A_2$ / Affinity", *J. Med. Chem.*, 34:1431–1435 (1991).
Buckle, et al., "Inhibition of Cyclic Nucleotide Phosphodiesterase by Derivatives of 1,3–Bis(cyclopropylmethyl)xanthine", *J. Med. Chem.* 37:476–485 (1994).
Dalpiaz, et al., "De Novo Analysis of Receptor Binding Affinity Data of Xanthine Adenosine Receptor Antagonists", *Arzneim–Forsch/drug Res.,* 230–233 (1995).
Bruns, "Adenosine Antagonism by Purines, Pteridines and Benzopteridines in Human Fibroblasts", *Biochemical Pharmacology*, 30:325–333 (1981).

(List continued on next page.)

*Primary Examiner*—Mark L. Berch
(74) *Attorney, Agent, or Firm*—McDonnell Boehnen Hulbert & Berghoff LLP

(57) ABSTRACT

A compound of the following formula:

(I)

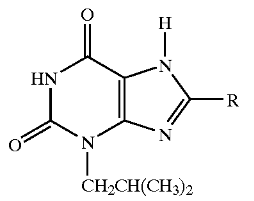

wherein R is an aliphatic or cycloaliphatic amine group or a pharmaceutically acceptable salt thereof and a pharmaceutically acceptable salt thereof. The compounds of formula (I) may be used to treat, among other indications, asthma and diarrhea.

8 Claims, 1 Drawing Sheet

OTHER PUBLICATIONS

Birdsall, et al., "Purine N–Oxides–XL The 3–Acyloxypurine 8–Substitution Recetion: Scope: Syntheses of 8–Substituted Xanthines and Guanines", *Tetrahedron*, 27:5969–5978 (1971).

Bergmann, et al., "Oxidaation of Hypoxanthines, Bearing 8–Aryl or 8–Pyridyl Substituent, by Bovine Milk Zanthine Oxidase", *Biochimica et Biophysica Acta*, 275–289 (1977).

Van der Wenden, et al.,. "Mapping the Xanthine C8–region of the adenosine $A_1$ Receptor with Computer Graphics," *European Journal of Pharmacology–Molecular Pharmacology Section*, 206:315–323 (1991).

Shimada, et al., "8–Polycycloalkyl–1,3–dipropylxanthines as Potent and Selective Antagonists for A1–Adenosine Receptors", *J. Med. Chem.*, 35:924–930 (1992).

Shimada, et al., "8–Dicyclopropylmethyl)–1,3–dipropylxanthine: A Potent and Selective Adenosine A1 Antagonist with Renal Protective and Diuretic Activities", *J. Med. Chem.*, 34:466–469.

Mosselhi, et al., "Reactions of some 8–diazoxanthine derivatives", *Indian Journal of Chemistry*, 33B:236–242 (1994).

* cited by examiner

SELECTIVE ANTAGONISTS OF A2B ADENOSINE RECEPTORS

This application claims the benefit of Provisional application No. 60/151,649, filed Aug. 31, 1999.

STATEMENT REGARDING FEDERALLY SPONSORED RESEARCH OR DEVELOPMENT

The present invention was made with the assistance of US Government funding (NIH Grant R29HL55596, N1H 1 PO1 HL56693). The US Government may have some rights in this invention.

FIELD OF THE INVENTION

The present invention relates to novel pharmaceutical compounds useful as selective antagonists of the $A_{2B}$ adenosine receptor. Furthermore, the present invention relates to novel pharmaceutical compositions useful for treating certain indications including asthma and diarrhea. The present invention also relates to novel methods of treating certain indications including asthma and diarrhea.

BACKGROUND OF THE INVENTION

There is substantial evidence that adenosine modulates many physiological processes. Its actions are mediated by interaction with specific cell membrane receptors. Four types of adenosine receptors have been identified: $A_1$, $A_{2A}$, $A_{2B}$ and $A_3$. All four subtypes have been cloned from human tissue. Adenosine receptors have the seven transmembrane domain structure typical of G protein-coupled receptors. Adenosine receptors are widely distributed throughout the body and are probably present in every cell.

Adenosine receptors were initially classified by the ability to inhibit ($A_1$) or activate ($A_2$ and $A_{2B}$) adenylate cyclase. $A_3$ receptors also inhibit adenylate cyclase. Modulation of adenylate cyclase is mediated through coupling to $G_s$ and $G_i$ guanine-nucleotide regulatory proteins. It is now known that adenosine receptors are also coupled to other intracellular signaling pathways. $A_1$ and $A_3$ receptors, for example, can couple to phospholipase C; $A_1$ receptors are also coupled to K channels. $A_{2B}$ receptors are also coupled to Gq and mediate activation of PLC, Ras and MAP kinases.

Substituted xanthines represent the most potent class of adenosine-receptor antagonists reported to date. See Katsushima et al., Structure-Activity Relationships of 8-cycloalkyl-1,3-dipropylxanthines as Antagonists of Adenosine Receptors, J. Med. Chem., 33:1906–1910 (1990); and Martinson et al., Potent Adenosine Receptor Antagonists that are Selective for the $A_1$ Receptor Subtype, Molecular Pharmacology, 31:247–252 (1987).

The study of $A_{2B}$ receptors has been hampered by the lack of selective pharmacological probes. Nonetheless, $A_{2B}$ receptors can be distinguished from $A_{2A}$ receptors by their low affinity and their distinct rank order of potency for agonists. NECA (5'-N-ethylcarboxamidoadenosine) is one of the most potent agonist at $A_{2B}$ receptors, but is also effective at $A_{2A}$ receptors. On the other hand, the agonist CGS 21680 (4-((N-ethyl-5'carbamoyladenos-2-yl)-aminoethyl)-phenylpropionic acid) is virtually inactive at $A_{2B}$ receptors, whereas it is as potent as NECA at $A_{2A}$ receptors. The lack of effectiveness of CGS 21680 has proven useful in the functional characterization of $A_{2B}$ receptors. $A_{2B}$ receptors also have a very low affinity to the $A_3$ selective agonists IB-MECA and $N^6$-benzyl NECA.

These agonists can, therefore, be used to differentiate between $A_{2B}$ and $A_3$ receptors. In summary, $A_{2B}$ receptors can be identified by their unique rank order of potency for agonists NECA>PIA≧IB-MECA>CGS-21680.

Whereas $A_{2B}$ receptors have, in general, a lower affinity for agonists compared to other receptors subtypes, this is not true for antagonists. The structure activity relationship of adenosine antagonists on $A_{2B}$ receptors has not been fully characterized, but at least some xanthines are as or more potent antagonists of $A_{2B}$ receptor subtypes than of other subtypes. In particular, DPSPX (1,3-dipropyl-8-sulphophenylxanthine), DPCPX and DPX (1,3 diethylphenylxanthine) have affinities in the mid to high nM range.

The present inventors have recognized that $A_{2B}$ receptors modulate important physiological processes. As stated by Feoktistov et al., Adenosine $A_{2B}$ Receptors as Therapeutic Targets, Drug Dev Res 45:198; $A_{2B}$ receptors have been implicated in mast cell activation, asthma, vasodialation, regulation of cell growth, intestinal function, and modulation of neurosecretion. Also see Feoktistov et al. Trends Pharmacol Sci 19:148–153.

Methods of mast cell activation, treating and/or preventing asthma and vasodialation, regulation of cell growth and intestinal function, and modulation of neurosecretion are all objects of the present invention.

As stated above, $A_{2B}$ receptors modulate important physiological processes. For example, $A_{2B}$ receptors are found in the colon in the basolateral domains of intestinal epithelial cells, and increase chloride secretion. Selective $A_{2B}$ antagonists with poor gastrointestinal absorption can also be useful in blocking intestinal chloride secretion. Thus, it is an object of the present invention to prevent and/or treat inflammatory gastrointestinal tract disorders including diarrhea.

Additionally, there are vascular beds in which NECA produces profound vasodilation. Based on reasonable confirmation that $A_{2B}$ receptors mediate vasodilation in the pulmonary circulation, an object of the present invention is to prevent and/or treat cardiac diseases.

$A_{2B}$ receptors are also present in cultured vascular smooth muscle cells and have been found to inhibit their growth. Since impaired adenosine mechanisms may play a role in the vascular remodeling process observed in atherosclerosis and hypertension, an object of the present invention is to prevent and/or treat atherosclerosis and hypertension.

$A_{2B}$ receptors are also present in endothelial cells and have been found to stimulate their growth. Since this will lead to growth of new blood vessels (angiogenesis). An object of this invention is to prevent and/or treat diseases characterized by abnormal blood vessel growth, such as diabetic retinopathy and cancer.

There is evidence that $A_{2B}$ receptors modulate mast cell function and that $A_{2B}$ receptors are present in mouse bone marrow-derived mast cells. $A_{2B}$ receptors have been shown to produce direct activation of HMC-1 cells, a cell line with phenotypic characteristics of human lung mast cells. This process involved activation of PLC through Gq proteins, and activation of MAP kinasis, intracellular processes not previously described for $A_2$ receptors. Virtually identical findings have been reported in a dog mastocytoma cells line. Evidence based on the research of the present inventors, using immunofluorescence techniques with a specific chicken anti-human $A_{2B}$ antibody, indicates the presence of $A_{2B}$ receptors in human lung mast cells obtained from asthmatics by bronchoalveolar lavage cells. Thus, an object of the present invention is to prevent and/or treat asthma.

Asthma continues to be a substantial medical problem that affects approximately 5–7% of the population. Despite advances in its treatment, the prevalence of asthma emergency department visits, hospitalizations, and mortality related to the disease, all appear to be on the rise.

Additionally adenosine treatments such as inhaled adenosine provokes bronchoconstriction in asthmatics, but not in normals. This process involves mast cell activation because it is associated with the release of mast cell mediators, including histamine, PGD2-β-hexosaminidase and tryptase, and because it can be blocked by specific histamine $H_1$ blockers and chromolyn sodium. Furthermore, adenosine has been shown to potentiate activation of purified human lung mast cells. The low affinity of this process suggests the involvement of $A_{2B}$ receptors. Given that inhaled adenosine has no effect in normals, there appears to be an intrinsic difference in the way adenosine interacts with mast cells from asthmatics. The in vitro response produced by $A_{2B}$ receptors in HMC-1 cells and in dog mastocytoma cells appears to mimic in vivo responses to inhaled adenosine in asthmatics, inasmuch as adenosine provokes mast cells activation in these cell lines as it does in asthmatics. Thus, an object of the present invention is a method of modulating mast cell function or activation of human lung cells.

Theophylline remains an effective antiasthmatic agent even though it is a poor adenosine receptor antagonist. However, considerable plasma levels are needed for it to be effective. Additionally, Theophylline also has substantial side effects, most of which are due to its CNS action, which provide no beneficial effects in asthma, and to the fact that it non-specifically blocks all adenosine receptor subtypes. The side effect profile of theophylline, therefore, can be improved substantially by generating selective and potent $A_{2B}$ antagonists such as the compounds of the present invention.

It is known that adenosine exhibits neurotransmitter depressing activity, bronchospasmic activity, bone absorption promoting activity, and the like via an $A_2$ receptor. Therefore, adenosine $A_2$ receptor antagonists are expected as therapeutic agents for various kinds of diseases caused by hyperergasia of adenosine $A_2$ receptors, for example, therapeutic agents for Parkinson's disease, anti-dementia agents, antidepressants, anti-asthmatic agents, and therapeutic agents for osteoporosis. Thus, an object of the present invention is providing such a therapeutic agent.

U.S. Pat. Nos. 4,352,956 and 4,804,664 to Kjellin et al. disclose the antiasthmatic drug enprofylline. Enprofylline has been discovered to be a relatively selective $A_{2B}$ antagonists. Enprofylline is of the following formula:

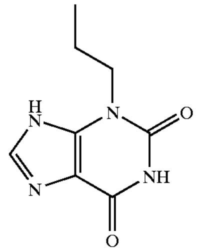

As is more fully described below, the compounds of the present invention have a potency much higher than enprofylline and are yet 40- to 60-fold selective compared to $A_{2A}$ and $A_1$.

DESCRIPTION OF THE PRIOR ART

As stated above, U.S. Pat. Nos. 4,325,956 and 4,804,664 to Kjellin et al. disclose xanthine derivatives including enprofylline used for the treatment of cardiac disease and chronic obstructive airway disease.

U.S. Pat. No. 4,089,959 to Diamond discloses xanthine derivatives useful for treating bronchial asthma and other bronchospastic diseases. More specifically, the xanthine derivatives 1,3,8-trialkylxanthines. Diamond discloses that the introduction of an alkyl group in the 8-position of the xanthine nucleus has been discovered to produce a compound having long lasting activity.

U.S. Pat. No. 4,120,947 to Diamond discloses 1,3-dialkyl-7-carbomethoxytheophylline xanthine derivatives useful in treating bronchospastic and allergic diseases. U.S. Pat. No. 4,120,947 discloses examples where xanthine derivatives with the carbomethoxy substituent at the 7-position shows greater activity than theophylline.

U.S. Pat. No. 5,641,784 to Kufner-Muel et al. discloses 1,3-dialkyl xanthine derivatives that may comprise an N-linked saturated 5- or 6-membered ring which may optionally contain oxygen or sulfur as a further heteroatom. The xanthine compounds are disclosed as being useful for the symptomatic therapy of degenerative disorders of the central nervous system such as, for example, senile dementia and Alzheimer's disease, Parkinson's disease, and traumatic brain injury.

U.S. Pat. No. 4,696,932 to Jacobson et al. discloses xanthine derivatives characterized by the presence of lower alkyl groups such as n-propyl groups at the 1 and 3 position on the theophylline ring and by a variety of para-substituents on a 8-phenyl ring. The compounds are disclosed as having significant activity as antiallergenic and antiasthmatic drugs as well as being useful in the treatment of cardiac and renal failure, high blood pressure, and depression.

Jacobson et al., Drug Rev Res 47:45–53 (1999) discloses 8-alkyl or 8-cycloalkyl xanthine derivatives that are described as being antagonists of $A_{2B}$ adenosine receptors. Jacobson et al. further disclose that the $A_{2B}$ AR subtype has been found to be involved in the control of cell growth and gene expression, vasodilatation, and fluid secretion from intestinal epithelia.

U.S. Pat. No. 5,877,180 to Linden et al. discloses xanthine derivative antagonists of $A_2$ adenosine receptors as being effective for the treatment of inflammatory diseases. Linden et al. further disclose that examples of the inflammatory diseases that may be treated according to U.S. Pat. No. 5,877,180 include ischemia, arthritis, asthma, multiple sclerosis, sepsis, septic shock, endotoxic shock, gram negative shock, toxic shock, hemorrhagic shock, adult respiratory distress syndrome, TNF-enhanced HIV replication and TNF inhibition of AZT and DDI activity, organ transplant rejection (including bone marrow, kidney, liver, lung, heart, skin rejection), cachexia secondary to cancer, HIV, and other infections, osteoporosis, infertility from endometriosis, cerebral malaria, bacterial meningitis, adverse effects from amphotericin B treatment, adverse effects from interleukin-2 treatment, adverse effects from OKT3 treatment, and adverse effects from GM-CSF treatment.

U.S. Pat. Nos. 5,670,498 and 5,703,085 to Suzuki et al., discloses xanthine derivative $A_2$ receptor antagonists useful as therapeutic agents for various kinds of diseases caused by hyperergasia of adenosine $A_2$ receptors, for example, therapeutic agents for Parkinson's disease, anti-dementia agents, anti-depressants, anti-asthmatic agents and therapeutic agents for osteoporosis.

U.S. Pat. No. 5,516,894 to Reppert discloses $A_{2B}$ antagonists that are useful as therapeutics to reduce inflammatory gastrointestinal tract diseases or asthma.

SUMMARY OF THE INVENTION

An object of the present invention is to provide a method for inhibiting activation of the $A_{2B}$ receptor by treating the receptor with a compound of the formula:

(I)

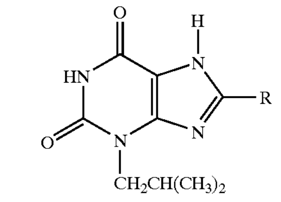

wherein R is an aliphatic or cycloaliphatic amine group. Preferably R is a $C_1$ to $C_6$ alkyl amine group, $C_1$ to $C_6$ dialkyl amine group, piperidino group, piperazino group, pyrrolino group, pyrrolidino group, a morpholino group, or an amino cyclohexyl derivative. More preferably, (II)

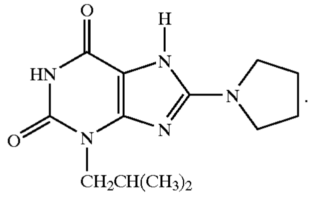

R is pyrrolidino as shown in the following formula:

It is another object of the present invention to provide a method of preventing and/or treating asthma, bronchospastic and allergic diseases as well as other obstructive airway-type diseases comprising administering a compound of the above-described formula (I). It is a further object of the present invention to provide a method for preventing and/or treating cardiac disease and Parkinson's disease comprising administering a compound of formula (I).

Other objects of the present invention include a method of antagonizing $A_{2B}$ receptors comprising administering to a mammal in need thereof an effective amount of a compound of formula (I); a method of treating asthma comprising administering to a mammal in need thereof an effective amount of a compound of claim 1; method of treating diarrhea comprising administering to a mammal in need thereof an effective amount of a compound of formula (I).

Furthermore, the present invention discloses a method of regulating at least one of smooth muscle tone, cell growth, intestinal function, and neurosecretion.

Another object of the present invention is to provide a method of treating inflammatory gastrointestinal tract disorders comprising administering to a mammal in need thereof an effective amount of a compound of formula (I).

Another object of the present invention is to provide for a method of treating Alzheimer's disease, Parkinson's disease, dementia, depression, or traumatic brain injury comprising administering to a mammal in need thereof an effective amount of compound of formula (I).

Another object of the present invention is to provide a method of treating inflammatory diseases comprising administering to a mammal in need thereof an effective amount of a compound of formula (I). The inflammatory diseases include asthma, multiple sclerosis, sepsis, septic shock, endotoxic shock, gram negative shock, toxic shock, hemorrhagic shock, adult respiratory disease syndrome, TNF-enhanced HIV replication, TNF inhibition of AZT and DDI activity, organ transplant rejection, cachexia secondary to cancer, HIV, osteoporosis, infertility from endometriosis, cerebral malaria, bacterial meningitis, adverse effects from amphotericin B treatment, adverse effects from interleukin-2 treatment, adverse effects from OKT3 treatment, and adverse effects from GM-CSF treatment.

The administration of a compound of formula (I) may be, for example, by oral, parenteral, or by inhalation mans in the form of tablets, capsules, solutions, elixirs, emulsions, aerosols, and the like. Typical effective doses in humans may range from, for example, from 0.2 to 10 milligrams per kilogram of body weight, preferably from 0.4 to 5 milligrams per kilogram, more preferably from 0.6 to 2 milligrams per kilogram, depending on the route of administration. However, the effective dose can be determined by one of ordinary skill in the art without undue experimentation.

DETAILED DESCRIPTION OF THE INVENTION

Figure 1:
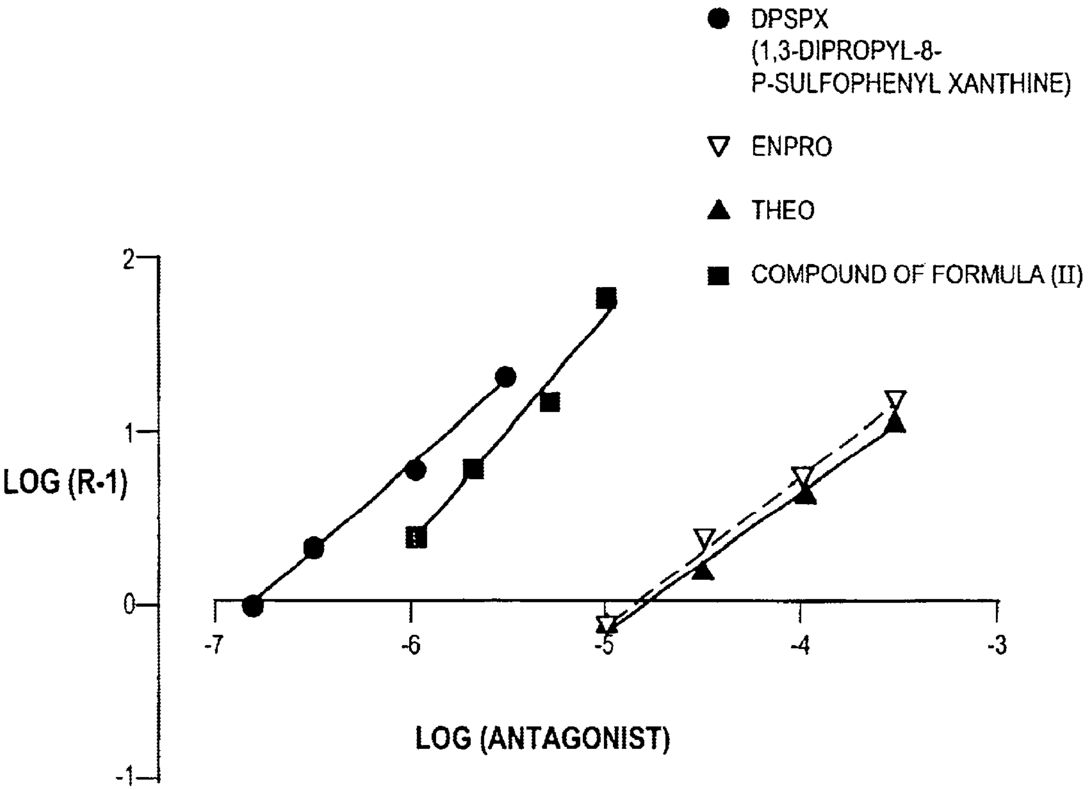
FIG. 1: A graph showing the antagonistic effects of xanthine derivatives on $A_{2B}$ receptors. A Schild analysis derived from dose-response curves for accumulation of cAMP produced by NECA in human erythroleukemia cells in the absence and in the presence of increasing concentrations of the antagonists. Schild analysis revealed a liner relationship for all compounds, suggesting competitive antagonism at $A_{2B}$ receptors. The intercept at the x-axis is an estimate of the Ki of the antagonists. The plot compares DPSPX, enprofylline, theophylline, and a compound of formula (II) of the present invention.

The present invention provides for a novel compound of the following formula:

(I)

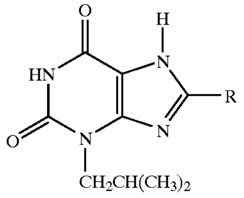

wherein R is an aliphatic or cycloaliphatic amine group. Preferably R is $C_1$ to $C_6$ alkyl amine group, $C_1$ to $C_6$ dialkyl amine group, piperidino group, piperazino group, pyrrolino group, pyrrolidino group, or a morpholino group, or an amino cycloxexyl derivative. Preferably the R group is bonded to the xanthine core at the nitrogen atom of the R group. Preferably the aliphatic or cycloaliphatic amine R group is a secondary amine group. More preferably, R is pyrrolidino as shown in the following formula:

(II)

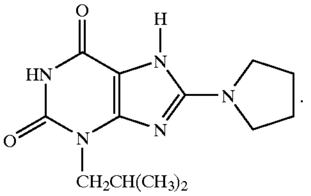

The present invention further provides for a compound of formula (I) or a pharmaceutically acceptable salt thereof being administered as part of a method of preventing and/or treating asthma. An additional embodiment of the present invention provides for a compound of formula (I) or a pharmaceutically acceptable salt thereof being administered as part of a method of preventing and/or treating diarrhea. Additional embodiments of the present invention include compound (I) or a pharmaceutically acceptable salt thereof being administered as part of a method of regulating smooth muscle tone, cell growth, intestinal function and neorosecretion.

Another embodiment of the present invention is to provide compounds (or pharmaceutically acceptable salts thereof or compositions that are useful as therapeutic agents for the various kinds of diseases caused by hyperergasia of adenosine $A_2$ receptors listed in U.S. Pat. No. 5,670,498 to Suzuki et al. such as, for example, Parkinson's disease, dementia, depression and osteoporosis.

For the purposes of this disclosure, a compound of formula (I) is understood to include the pharmaceutically acceptable salt(s) thereof. The pharmaceutically acceptable salts of a compound of formula (I) include, for example, pharmaceutically acceptable acid additional salts, metal salts, ammonium salts, organic amine addition salts, amino acid addition salts.

Preferred pharmaceutically acceptable acid addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaric acid, oxalic acid, and the like; and salts to tribasic carboxylic acids, such as, carboxysuccinic acid, citric acid, and the like. Further examples of the pharmaceutically acceptable salts that may be used as forms of a compound of formula (I) of the present invention includes those disclosed in U.S. Pat. No. 5,870,180 to Linden et al.; U.S. Pat. No. 5,780,481 to Jacobsen et al.; U.S. Pat. No. 4,325,956 to Kjellin et al.; and U.S. Pat. No. 5,670,498 to Suzuki et al.

In the methods of the present invention, the $A_{2B}$ adenosine receptor antagonists herein described form the active ingredient, and are typically administered in an admixture with suitable pharmaceutical diluents, excipients or carriers (collectively referred to as "carrier" materials) suitably selected with respect to the intended form of administration (i.e., oral tablets, capsules, inhalers, syrups, etc.), and consistent with conventional pharmaceutical practices.

A compound of formula (I) may be prepared as follows: A 1-H-3-isobutylxanthine compound is used as a starting material (see K. R. H. Wooldrige and R. Slack, J Chem. Soc., 1863 (1962)). The 1-H-3-isobutylxanthine compound is brominated as described for the preparation of 1-methyl-3-isobutyl-8-bromoxanthine (see G. L. Kramer, J. E. Garst, and J. N. Wells, Biochemistry, 16:3316 (1977)). Compounds of formula (I) are prepared by reaction of 1-H-3-isobutylxanthine with the corresponding secondary amine (i.e., the R group of formula (I)), as described for the preparation of 1,3-dipropyl-8-pyrrolidinoxanthine (see T. Katsushima, L. Nieves, and J. N. Wells, J.Med. Chem. 33:1906–1910 (1990)).

In clinical practice, the compounds and compositions of the present invention will normally be administered orally, rectally, nasally, sublingually, by injection or by inhalation.

For example, compounds of formula (I) and/or pharmaceutically acceptable salts thereof can be administered as they are, or in the form of various pharmaceutical compositions. The pharmaceutical compositions in accordance with the present invention can be prepared by uniformly mixing an effective amount of a compound of formula (I) and/or a pharmaceutically acceptable salt thereof, as an active ingredient, with a pharmaceutically acceptable carrier. If oral administration is desired, for example, preferably such pharmaceutical compositions are prepared in a unit dose form suitable for oral administration.

For preparing a pharmaceutical composition of the present invention for oral administration, any useful pharmaceutically acceptable carrier can be used. That is, the particular pharmaceutically acceptable carrier is not known to be critical. In fact, the only limitation as to the materials used in preparing the compositions of the present invention us that the materials should be pharmaceutical pure and non-toxic in the amounts used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservations such as p-hydroxybenzoates, flavors such strawberry flavor and peppermint, and the like. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules may be the most useful oral unit dose forms because of the readiness of administration. For preparing tablets and capsules, solid pharmaceutical carriers are preferably used.

The compounds of formula (I) can be administered orally, for example, with an inert diluent with an edible carrier. They can be enclosed in gelatin capsules or compressed into tablets. For the purpose of oral therapeutic administration, the compounds can be incorporated with excipients and used in the form of tablets, troches, capsules, elixirs, suspensions, syrups, waters, chewing gums, and the like. These preparations should preferably contain at least 0.5% by weight of a compound of formula (I), but may be varied between about 0.05% to about 10%, more preferably between 0.1% and about 5% by weight, depending upon the particular form. The amount of the compound of formula (I) in such compositions is such that a suitable dosage will be obtained.

Tablets, pills, capsules, troches, and the like may further comprise the following ingredients: a binder, such as microcrystalline cellulose, gum tragacanth or gelatin; an excipient, such as starch or lactose; a disintegrating agent, such as alginic acid, Primogel, corn starch, and the like; a lubricant, such as magnesium stearate or Sterotes; a glidant, such as colloidal silicon dioxide; a sweetening agent, such as sucrose, saccharin or aspartame; or flavoring agent, such as peppermint, methyl salicylate, or flavoring such as orange flavoring. When the dosage unit form is a capsule it may further comprise, in addition to the compound of formula (I), a liquid carrier, such as a fatty oil.

Other dosage unit forms can further comprise other materials that modify the physical form of the dosage unit, for example, as coatings. Thus, tablets or pills can be coated with sugar, shellac, or other enteric coating agents. A syrup may contain, in addition to the active compounds, sucrose as a sweetening agent and preservatives, dyes, colorings and flavors. For purposes of parenteral therapeutic administration, the compounds of formula (I) can be incorporated into a solution or suspension. These preparations should preferably contain at least 0.05% of the aforesaid compound, but may be varied between 0.01% and 0.4%, more preferably between 0.8 % and 0.1 % of the weight thereof. The amount of active compound in such compositions is such that a suitable dosage will be obtained.

Injectable preparations can be prepared using a carrier such as distilled water, a salt solution, a glucose solution or a mixture of a salt solution, suspension, or dispersion according to a conventional method by using a suitable solubilizing agent or suspending agent. Solutions or suspensions of the compound of formula (I) can also include the following components: a sterile diluent, such as water for injection, saline solution, fixed oils, polyethylene glycols, glycerine, propylene glycol or other synthetic solvents: antibacterial agents, such as benzyl alcohol or methyl parabens; antioxidants, such as ascorbic acid or sodium bisulfite; chelating and agents, such as ethylenediaminetetraacetic acid; buffers such as acetates, citrates or phosphates; and agents for the adjustment of tonicity, such as sodium chloride or dextrose. The parenteral preparation can be enclosed in ampoules, disposable syringes or multiple dose vials made of glass or plastic.

Compounds of formula (I) may also be administered by inhalation in the form of aerosol, fine powder, or spray solution. In the case of aerosol administration, the compound of the present invention is dissolved in an appropriate pharmaceutically acceptable solvent such as, for example, ethyl alcohol or a combination of miscible solvents, and the resulting solution is mixed with a pharmaceutically acceptable propellant. Commercially available nebulizers for liquid formulations, including jet nebulizers and ultrasonic nebulizers are useful for such administration. Liquid formulations can be directly nebulized and lyophilized powder can be nebulized after reconstitution. For administration by inhalation, the antagonists are conveniently delivered in the form of an aerosol spray presentation from pressurized packs or nebulizers. The compounds may also be delivered as powders which may be formulated and the powder composition may be inhaled with the aid of an insufflation powder inhaler device.

The effective dose and the administration schedule vary depending upon the mode of administration, the age, body weight, and conditions of a patient, etc. However, generally, compounds of formula (I) or a pharmaceutically acceptable salt thereof is administered in a daily dose of 6 to 800 mg, preferably from 12 to about 400 mg, and more preferably from 18 to 160 mg.

Other features of the invention will become apparent in the course of the following examples which are given for illustration of the invention and are not intended to be limiting thereof.

EXAMPLE 1

This Example illustrates how the compounds of the invention may be incorporated in pharmaceutical compositions.

| Aerosol for Inhalation | |
|---|---|
| Active substance | 1.50 g |
| "Miglyol" (Registered Trade Mark) | 0.02 g |
| "Frigen" (Registered Trade Mark) 11/12/13/114 | ad 100.0 g |

-continued

"Frigen" is used to denote the halogenated hydrocarbons. "Frigen" 114 is 1,2-dichloro-1,1,2,2-tetrafluorethane, "Frigen" 113 is 1,1-difluoro-2,2-dichlorotrifluorotrichlorethane, "Frigen" 11 is trichloromonofluoromethane and "Frigen" 12 is dichlorodifluoromethane. "Miglyol" denotes a triglyceride of saturated vegetable oils. Or a pulver aerosol where the active substance is mixed with lactose.

| Tablets | |
|---|---|
| Active substance | 20.0 mg |
| Maize starch | 25.0 mg |
| Lactose | 190.0 mg |
| Gelatin | 1.5 mg |
| Talc | 12.0 mg |
| Magnesium stearate | 1.5 mg |
| | 350. mg |

| Suppositories | |
|---|---|
| Active Substance | 50.0 mg |
| Ascorbyl palmitate | 1.0 mg |
| Suppository base (Imhausen H) | ad 2000.0 mg |

| Injection Solution | |
|---|---|
| Active substance | 2.000 mg |
| Sodium hydroxide | 0.310 mg |
| Sodium purosulphite | 0.500 mg |
| Disodium edetate | 0.100 mg |
| Sodium chloride | 8.500 mg |
| Sterile water for injection | ad 1.00 g |

EXAMPLE 2

This example compares the potency and selectivity towards various adenosine receptors of a compound of formula (I) wherein R is pyrrolidino to the potency and selectivity of theophylline, DPSPX (1,3-dipropyl-8-p-sulfophenylxanthine), and enprofylline.

Antagonist potency ($K_1$ or $K_B$, $\mu$M)

| Compound | $A_1$ Receptor | $A_{2A}$ Receptor | $A_{2B}$ Receptor | $A_3$ Receptor |
|---|---|---|---|---|
| Theophylline | 8.5[1] (r) | 25[2] (r) | 5[3] (h) | >100[9] (r) |
| DPSPX | 0.14[1] (r) | 0.79[2] (r) | 0.14[3] (h) | >100[9] (r) |
| Enprofylline | 156[4] (h) | 32[5] (h) | 7[3.6] (h) | 56[10] (h) |
| Formula (I) | 31[7] (h) | 20[8] (h) | 0.525[3] (h) | 53[11] (h) |

[1]Displacement of [$^3$H] PIA binding from rat brain membranes. (See A. S. Rovena et al. Drug Dev. Res. 39: 243–252 (1996) and Ukena et al. Febs Letters 209: 122–128 (1986)).

[2]Displacement of [$^3$] CGS 21680 from rat striatal membranes. (See I. Hide et al. Mol. Pharmacol. 41: 352–359 (1992)).

-continued

| | Antagonist potency ($K_I$ or $K_B$, $\mu M$) | | | |
|---|---|---|---|---|
| Compound | $A_1$ Receptor | $A_{2A}$ Receptor | $A_{2B}$ Receptor | $A_3$ Receptor |

[3]Inhibition of NECA-stimulated cAMP in HEL cells. (See I. Feoktistov and I. Biaggioni. Mol. Pharmacol. 43: 909–914 (1993)).
[4]Displacement of [$^3$H] DPCPX from membranes of HEK-293 cells transfected with human $A_1$. (See J. Linden et al. Life Science. 62: 1519–1524 (1998)).
[5]Displacement of [$^3$H] CGS 21680 from membranes of HEK-293 cells transfected with human $A_{2A}$. (See A. S. Rovena et al. Drug Dev. Res. 39: 243–252 (1996)).
[6]Displacement of [$^3$H] 1,3-diethyl-8-phenylxanthine from membranes of HEK-293 cells transfected with human $A_{2A}$. (See A. S. Rovena et al. Drug Dev. Res. 39: 243–252 (1996)).
[7]Displacement with [$^3$] DPCPX from membranes of CHO cells transfected with human $A_1$. (See K. N. Klotz, et al. N-S Arch. Pharmacol. 357: 1–9 (1998))
[8]Inhibition of CGS 21680-stimulated cAMP in HMC-1 cells. (See I. Feoktistov, and I. Biaggioni, Biochem. Pharmacol. 55: 627–633 (1998)).
[9]Displacement of [125I] APNEA from membranes of CHO cells transfected with rat A3 (see P. J. van Galen, et. al. Mol. Pharmacol. 45: 1101–1111 (1994)).
[10]Displacement of [125I] ABA from membranes of HEK-293 cells transfected with human A3 (see J. A. Auchampach, et al. Mol. Pharmacol. 52: 846–860 (1997)).
[11]Displacement of [3H] NECA from CHO cells transfected with human A3 (see K. N. Klotz, et al. N-S. Arch Pharmacol. 357: 1–9 (1998)).

As can be seen from the above table, compounds of formula (I) wherein R is pyrrolidino have potencies much higher than that of enprofylline, for example, and are 40- to 60-fold selective compared to $A_{2A}$ and $A_1$.

All cited patents and publications referred to in this application are herein expressly incorporated by reference.

This invention thus being described, it will be obvious that the same may be varied in many ways. Such variations are not to be regarded as a departure from the spirit and scope of the present invention, and all such modifications as would be obvious to one of ordinary skill in the art are intended to be included within the scope of the following claims.

We claim:

1. A method of treating diarrhea comprising administering to a mammal in need thereof an effective amount of a compound of the following formula:

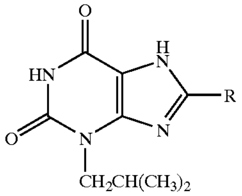

wherein R is selected from $C_1$ to $C_6$ alkyl amine, $C_1$ to $C_6$ dialkyl amine, unsubstituted piperidino, piperazino, pyrrolidino, pyrrolino, morpholino, or a pharmaceutically acceptable salt thereof.

2. A method of treating inflammatory gastrointestinal tract disorders comprising administering to a mammal in need thereof an effective amount of a compound of the following formula:

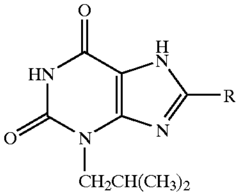

wherein R is selected from $C_1$ to $C_6$ alkyl amine, $C_1$ to $C_6$ dialkyl amine, unsubstituted piperidino, piperazino, pyrrolidino, pyrrolino, morpholino, or a pharmaceutically acceptable salt thereof.

3. A method of treating depression, comprising administering to a mammal in need thereof an effective amount of a compound of the following formula:

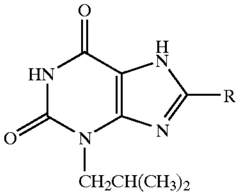

wherein R is selected from $C_1$ to $C_6$ alkyl amine, $C_1$ to $C_6$ dialkyl amine, unsubstituted piperidino, piperazino, pyrrolidino, pyrrolino, morpholino, or a pharmaceutically acceptable salt thereof.

4. The method of claim 1 or 2 or 3, wherein said compound is incorporated with inert carriers into a tablet and administered orally.

5. The method of claim 1 or 2 or 3, wherein said compound is incorporated with a propellant and a solvent and administered by inhalation of mist.

6. The method of claim 1 or 2 or 3, wherein said compound is incorporated with a pharmaceutically acceptable carrier and injected into said mammal.

7. A compound having the following formula:

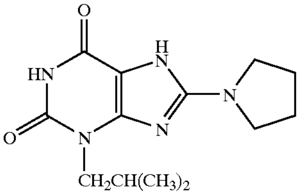

or a pharmaceutically acceptable salt thereof.

8. A method of treating asthma comprising administering to a mammal in need thereof an effective amount of a compound of the following formula:

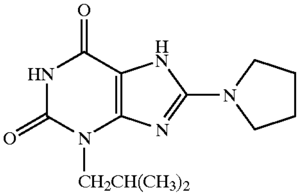

or a pharmaceutically acceptable salt thereof.

* * * * *